(12) United States Patent
Zhang et al.

(10) Patent No.: US 9,820,652 B2
(45) Date of Patent: Nov. 21, 2017

(54) MULTI-PHOTON MICROSCOPE HAVING AN EXCITATION-BEAM ARRAY

(71) Applicant: The Board of Trustees of the Leland Stanford Junior University, Palo Alto, CA (US)

(72) Inventors: Tong Zhang, Palo Alto, CA (US); Mark Schnitzer, Palo Alto, CA (US); Jerome Anthony-Jean Lecoq, Menlo, CA (US); Joan Savall, Palo Alto, CA (US); Hyun Kim, Menlo Park, CA (US); Oleg Rumyantsev, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 389 days.

(21) Appl. No.: 14/562,885

(22) Filed: Dec. 8, 2014

(65) Prior Publication Data
US 2015/0157210 A1    Jun. 11, 2015

Related U.S. Application Data

(60) Provisional application No. 61/913,695, filed on Dec. 9, 2013.

(51) Int. Cl.
*A61B 5/00* (2006.01)
*G02B 21/00* (2006.01)
*G01N 21/64* (2006.01)

(52) U.S. Cl.
CPC .......... *A61B 5/0071* (2013.01); *A61B 5/4064* (2013.01); *G01N 21/6458* (2013.01); *G02B 21/0032* (2013.01); *G02B 21/0076* (2013.01); *A61B 5/0042* (2013.01)

(58) Field of Classification Search
CPC ... A61B 5/0042; A61B 5/0071; A61B 5/4064; G01N 21/6458; G02B 21/0032; G02B 21/0076
See application file for complete search history.

(56) References Cited

U.S. PATENT DOCUMENTS

| 8,284,483 | B2 | 10/2012 | Beaurepaire et al. |
| 2007/0057211 | A1 | 3/2007 | Bahlman et al. |
| 2012/0257196 | A1 | 10/2012 | Raicu et al. |

OTHER PUBLICATIONS

David S. C. Biggs et al., "Acceleration of Iterative Image Restoration Algorithms", Mar. 10, 1997, pp. 1766-1775, vol. 36, No. 8, Publisher: Applied Optics.

*Primary Examiner* — Michael Rozanski
(74) *Attorney, Agent, or Firm* — Kaplan Breyer Schwarz, LLP (57) ABSTRACT

A two-photon imaging system capable of imaging of an image region in real time is presented. The imaging system comprises a source of excitation light that provides the excitation light as a plurality of laser beamlets. The plurality of laser beamlets is collectively scanned by a single-axis scanner along a first direction in the focal plane of the image region and oriented such that neither the rows nor columns are aligned with the first direction. As a result, each laser beamlet scans a different sub-region of the image region and the plurality of sub-regions are simultaneously scanned. As a result, the entirety of the image region is scanned in the same amount of time required to scan one image sub-region.

17 Claims, 8 Drawing Sheets

MULTI-PHOTON MICROSCOPE HAVING AN EXCITATION-BEAM ARRAY

CROSS REFERENCE TO RELATED APPLICATIONS

This case claims priority of U.S. Provisional Patent Application Ser. No. 61/913,695, filed Dec. 9, 2013, which is incorporated by reference. If there are any contradictions or inconsistencies in language between this application and one or more of the cases that have been incorporated by reference that might affect the interpretation of the claims in this case, the claims in this case should be interpreted to be consistent with the language in this case.

FIELD OF THE INVENTION

The present invention relates to microscopy in general, and, more particularly, to multi-photon microscopy.

BACKGROUND OF THE INVENTION

Multi-photon microscopy is an imaging technique in which an excitation laser signal is scanned over a region of interest (i.e., image field) and fluorophores in the image field are excited only when they simultaneously absorb multiple photons of the excitation light. In two-photon microscopy, for example, simultaneous absorption of two photons is required to excite a fluorophore. Multi-photon microscopy is often used to generate fluorescent images of living cells and other microscopic objects and has become an important tool in medical imaging.

Multi-photon microscopy enables imaging of living tissue at depths to about one millimeter (mm). Because longer wavelengths tend to scatter in tissue to a lesser degree than shorter wavelengths, the excitation laser typically provides a signal characterized by an infrared wavelength. To excite the dye to emit a fluorescence photon, two photons of infrared light must be absorbed simultaneously. Infrared excitation light is attractive because it minimizes scattering in the tissue being imaged. In order to create a two-dimensional image of the image field, the laser beam is scanned over the image field while fluorescence light from each point in the region is detected at a camera or photo-multiplier tube.

Fluorescent emission from the fluorophores increases quadratically with the intensity of the excitation light. As a result, by strongly focusing the excitation signal, fluorescence can be confined within a narrow focal depth. This gives a depth-of-field resolution comparable to that produced by conventional confocal laser scanning microscopes.

Unfortunately, conventional two-photon microscopy technology suffers from relatively low imaging speeds (typically within the range of 10-20 Hz) because it is difficult to gather sufficient numbers of photons from each pixel at high frame rate. For example, a Ti-Sapphire laser is a commonly used excitation source. Unfortunately, commercially available Ti-Sapphire lasers have an average power of only a few Watts and a repetition rate of around only 80 MHz. This enables a photon collection rate of approximately 100-10,000 photons per pixel, per image frame, and at a frame rate of no more than 10-20 Hz—resulting in a signal-to-noise ratio (SNR) of only 10-100. A higher frame rate could potentially be achieved by simply increasing the scanning speed of the excitation signal (e.g., by 100-fold). Unfortunately, operation at a higher frame rate results in reduced photon collection (to only ~1-10 photons per pixel per frame). As a result, the deleterious effects of faster scanning on image quality and SNR generally outweigh any potential benefit. Furthermore, in practice, scanning speed is often limited by mechanical and/or optical constraints.

Other comparable microscopy technologies capable of high frame rate are also beset by several disadvantages. Conventional single-photon epifluorescence microscopy suffers from high tissue scattering and low optical sectioning ability. Such disadvantages can give rise to an overlap of photons emitted from different positions into the same pixel of the camera leading to significant image blur, thereby degrading image resolution. Line scanning two-photon microscopy and random access two-photon microscopy with acousto-optic deflector can achieved single focus two-photon scanning at higher frame rate, however at the cost of sacrificing number of pixels being imaged down to a single line of pixels and limited number of arbitrarily selected pixels in focal plane, respectively.

A two-photon imaging system that can provide an image of a region of interest in real time and with improved clarity would be a significant advance in the state-of-the-art.

SUMMARY OF THE INVENTION

The present invention enables imaging of a large image region in real time by linearly scanning an array of interrogation beams across the image region, where the array is rotated in the plane of the image region so that, within a single scan, each beamlet interrogates a different one of a two-dimensional array of linear sub-regions and the entire image region is interrogated. Embodiments of the present invention are particularly well suited for use in in-vivo brain imaging, simultaneous multi-area imaging of disparate brain subsystems, and simultaneous surface- and deep-imaging. The present invention is applicable to multi-photon microscopy and single-photon microscopy.

An illustrative embodiment comprises a two-photon microscopy imaging system that employs an optical system that provides a plurality of laser beamlets arranged such that give rise to a two-dimensional array of optical spots (i.e., foci) at an image region that defines a first plane, where the array includes a plurality of rows of foci. The beamlets simultaneously excite fluorescence at a two-dimensional array of locations that are distributed throughout the image region. The imaging system linearly scans the beamlet array across the image region in a first direction, where the beamlet array is oriented with respect to the first direction such that each of its rows forms an angle to the first direction. The angle, the number of beamlets, and the beamlet spacing within each row are selected so that adjacent beamlets in each row are staggered along the spacing between the rows in the direction orthogonal to the scan direction. As a result, high-resolution scanning of the entire image region during a single linear scan of the beamlet array is enabled, where each beamlet interrogates a different linear sub-region of the total image region. Further, a large image region can be interrogated in the same amount of time required to scan each much smaller imaging sub-region. Because the entire image region is scanned during each linear scan of the beamlet array, only a single-axis scanner is required. Embodiments of the present invention, therefore, have lower complexity and cost than multi-photon microscopy systems of the prior art.

In some embodiments, the angle, the number of beamlets, and the beamlet spacing within each row are selected so that adjacent beamlets in each row are substantially evenly distributed along the spacing between the rows in the direction orthogonal to the scan direction. In some embodiments, the spacing of the beamlets and the angle of rotation of the array are selected such that the spacing between adjacent scan lines is sufficiently small to achieve micron-level image resolution, while also keeping the spacing between the spots large enough to mitigate crosstalk.

In some embodiments, the excitation source is an ultrashort-pulsed regenerative fiber laser amplifier, which enables each laser pulse to have an energy higher than that provided by a Ti-Sapphire laser, which is typically used in the prior art. The higher energy of the laser pulses enables an enhanced two-photon excitation effect for each of the plurality of laser foci, yet the ultrashort-pulsed operation keeps the average optical power delivered to brain tissue within a tolerable level.

In some embodiments, a deconvolution algorithm is used to reconstruct a complete image frame from multiple sub-frames. In some embodiments, the deconvolution algorithm includes additional correction for optical cross-talk between neighboring laser foci.

An embodiment of the present invention is an imaging system comprising: a source operative for providing a first plurality of light signals the first plurality of light signals being arranged such that they form a two-dimensional array of foci at an image region that defines a first plane; a single-axis scanner operative for linearly scanning the first plurality of light signals along a first direction in the first plane such that each light signal of the first plurality thereof interrogates a different one of a plurality of sub-image regions, wherein the plurality of sub-image regions are arranged in a two-dimensional arrangement within the image region; and a detector operative for detecting a second plurality of light signals, wherein each of the second plurality of light signals is generated in response to absorption of optical energy from at least one of the first plurality of light signals.

DETAILED DESCRIPTION

Figure 1:
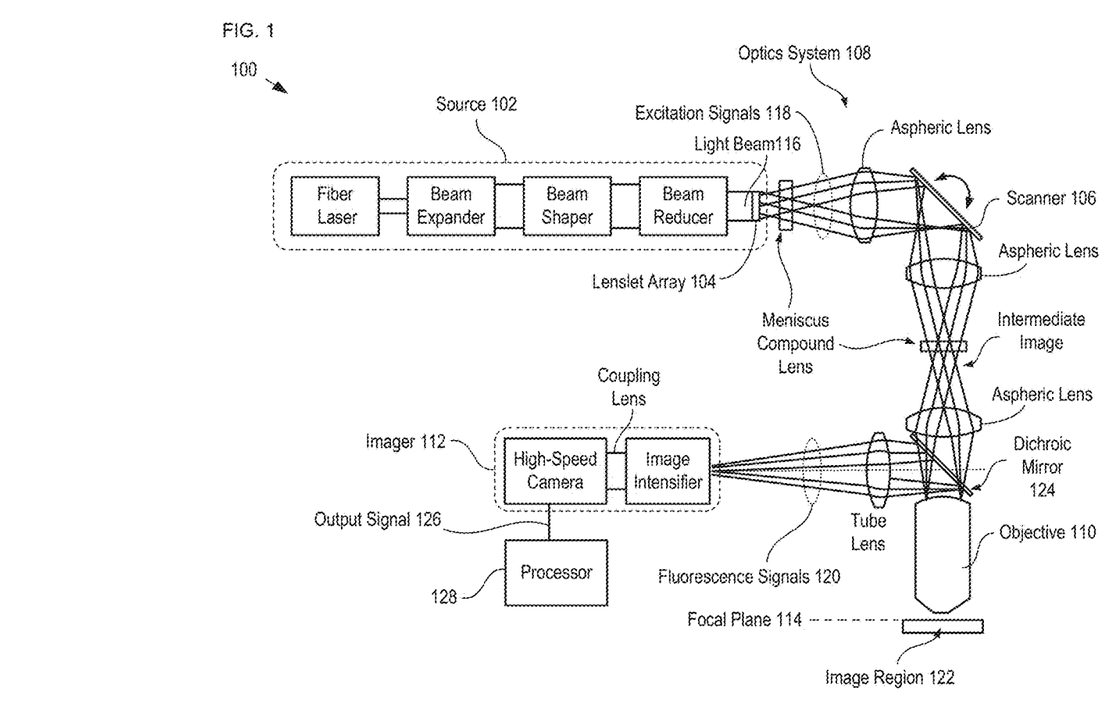
FIG. 1 depicts a schematic drawing of a portion of an imaging system in accordance with an illustrative embodiment of the present invention.

FIG. 1 depicts a schematic drawing of a portion of an imaging system in accordance with an illustrative embodiment of the present invention. Imaging system 100 is a two-photon laser-scanning microscopy system that comprises source 102, lenslet array 104, scanner 106, optics system 108, objective 110, imager 112, and processor 128. In some embodiments, imaging system 100 is a single-photon microscopy system. In some embodiments, imaging system 100 is a multi-photon microscopy system that requires more than two photons to excite a fluorophore.

Figure 2:
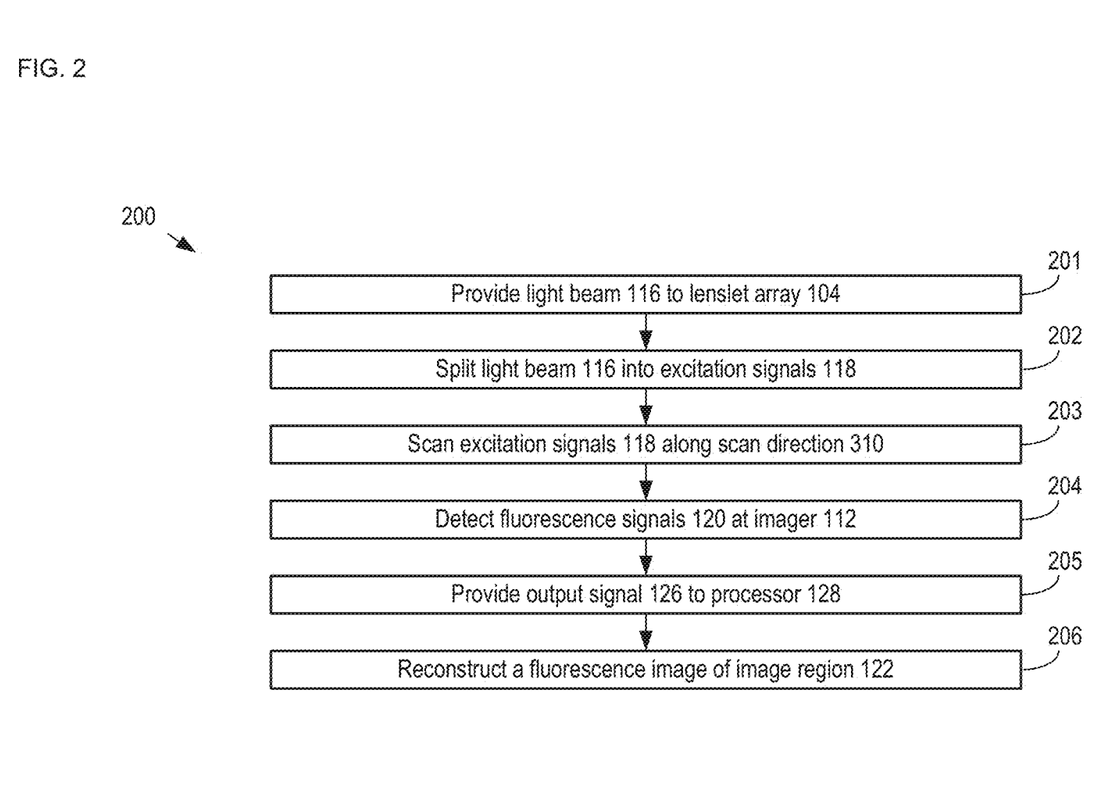
FIG. 2 depicts operations of a method suitable for imaging an image region in accordance with the illustrative embodiment of the present invention.

FIG. 2 depicts operations of a method suitable for imaging an image region in accordance with the illustrative embodiment of the present invention. Method 200 begins with operation 201, wherein light beam 116 is provided to lenslet array 104.

Source 102 includes an ultrashort-pulsed regenerative fiber laser amplifier (hereinafter referred to as a "fiber laser") that emits light at approximately 1030 nm (e.g., a regenerative ultrafast $Yb^{3+}$ laser amplifier, etc.). The fiber laser has an average power of 20 Watts and a tunable repetition rate that is within the range of approximately 200 kHz to approximately 2 MHz. As a result, the fiber laser provides pulses of optical energy that have higher energy than the typical output power of a conventional Ti-Sapphire laser. This enables an enhancement of the two-photon excitation effect for multiple laser foci in each of excitation signals 118; however, it keeps the average optical power delivered to image region 122 within a tolerable range.

At operation 202, lenslet array 104 distributes the optical energy in light beam 116 into excitation signals 118 (i.e., beamlets 118) and provides them to optics system 108.

Lenslet array 104 is an array of microlenses operative for receiving light beam 116 and distributing it into a two-dimensional array of equal-intensity beamlets (i.e., excitation signals 118). In order to convert the output of the fiber laser into a plurality of substantially equal-intensity beamlets, prior to being received by lenslet array 104, the output of the fiber laser is first expanded and then shaped at a beam shaper, which corrects the beam profile from Gaussian to flat. Once corrected, the now homogeneous-intensity laser beam is reduced again and provided to lenslet array 104. The lenslet array splits the laser beam into a plurality of beamlets. In the illustrative embodiment, excitation signals 118 includes 25 beamlets; however, the number of beamlets can have any practical value. Excitation signals 118 typically includes hundreds of beamlets.

Optics system 108 is an arrangement of optical components for providing excitation signals 118 as a two-dimensional array of foci at focal plane 118. Optics system 108 includes numerous optical components, including aspheric lenses, meniscus compound lenses for mitigating field curvature at focal plane 118, dichroic mirror 124 for removing light at the excitation wavelength from the light received at imager 112, a tube lens, and scanner 106. It should be noted that the design and arrangement of optics system 108 depicted in FIG. 1 is merely exemplary and that myriad alternative designs and arrangements suitable for use in the present invention would be readily realizable for one of ordinary skill in the art.

Figure 3A:
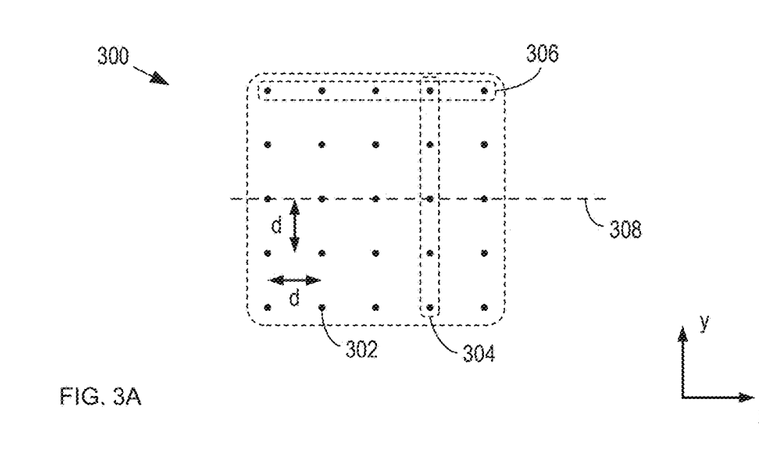
FIG. 3A depicts a portion of foci array 300 at focal plane 114.

FIG. 3A depicts a portion of foci array 300 at focal plane 114.

Foci array 300 is a two-dimensional array of foci 302, which are arranged in equally spaced columns 304 and rows 306. The x- and y-spacing, d, between adjacent foci 302 at focal plane 114 is equal and has a value of approximately 25 microns; however, one skilled in the art will recognize that the spacing can have any suitable value. In some embodiments, the x- and y-spacing between foci 302 is different. Each of rows 306 is parallel with array axis 308.

Scanner 106 is a single-axis laser scanning mirror. In some embodiments, scanner 106 is a different scanning element, such as a rotatable prism, dual-axis scanning mirror configured to scan in only one dimension, and the like. The positions of scanner 106 and the aspheric lenses within optics system 108 are selected such that each of excitation signals 118 is incident on the center of scanner 106 as well as the back aperture of objective 110.

It is an aspect of the present invention that the use of a single-axis scanning element affords advantages over multi-photon imaging systems of the prior art, which include dual-axis scanners that raster scan a light beam over an image region. A single-axis scanning element can operate at a modest rate (e.g., the same as the frame rate of the system) and requires a relatively simple controller.

In contrast, a conventional raster-scanning mechanism requires that the fast-scanning axis operates at a much higher rate than the imaging frame rate. This need for high-speed scanning makes it extremely difficult, if not impossible, for such a scanner to work properly. For example, a typical prior-art high-speed mechanical scanner capable of kHz (or higher) operation operates in resonance mode. As a result, such prior-art scanners are normally characterized by relatively poor angular position control, which gives rise to poor image resolution for their corresponding microscope systems.

Figure 3B:
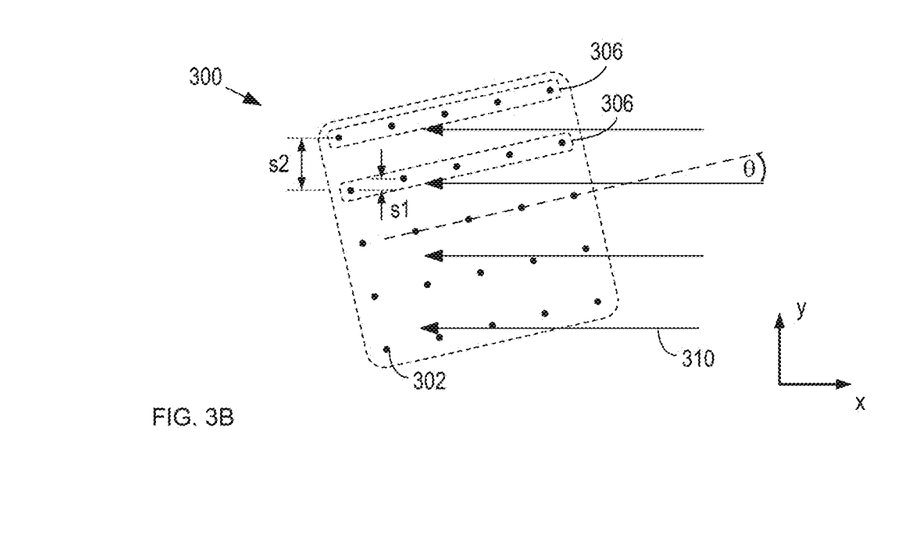
FIG. 3B depicts a portion of foci array 300 at focal plane 114 where the array is rotated by angle, θ, relative to the scanning direction 310 of scanner 106.

At operation 203, scanner 106 scans excitation signals 118 along scan direction 310 (i.e., along the x-direction as shown in FIGS. 3A-B). In some embodiments, the scanner scans the excitation signals through the desired range of motion in approximately 1 millisecond.

Scanner 106 and optics system 108 are arranged such that foci array 300 is rotated relative to the array of beamlets in excitation signals 118 so that the scanner scans the beamlets along a direction that is at a non-zero angle with respect to the direction defined by the rows of beamlets.

FIG. 3B depicts a portion of foci array 300 at focal plane 114 where the array is rotated by angle, $\theta$, relative to the scanning direction 310 of scanner 106. Foci array 300 is tilted relative to the scan direction of scanner 106 to enable foci 306 to collectively scan the entirety of image region 122.

The value of $\theta$ is based on the spacing between foci 302 as well as the number of foci in each row 306, N. In some embodiments, $\theta$ is equal to arctan (1/N). The values of angle, $\theta$, and spacing, d, are selected so that the spacing between adjacent scanning lines is small enough to enable a desired spatial resolution (e.g., micron-level resolution). In some embodiments, these values are selected to mitigate crosstalk as well. In some embodiments, the values of angle, $\theta$, and spacing, d, are selected so that, along the direction orthogonal to scanning direction 310 (i.e., along the y-direction as shown in FIGS. 3A-B), the separation, s1, between adjacent foci within each row 306 is an even fraction of the separation, s2, between adjacent rows 306.

At operation 204, fluorescence signals 120 are detected at imager 112, which generates output signal 128 based on the fluorescence signals. Fluorescence signals 120 are generated at fluorophores located in image region 122. As fluorescence signals 120 are emitted from image region 122, they are incident on dichroic mirror 124, which passes reflected light at the excitation wavelength but reflects light at fluorescence wavelengths toward imager 112.

Imager 112 is a multi-pixel photon collecting device characterized by noise that is nearly shot-noise-limited. Imager 112 enables simultaneous capture of fluorescence signals from substantially all excited fluorophores in image region 122.

In the illustrative embodiment, exemplary imager 112 comprises an image intensifier and high-speed camera operative for directly forming multi-pixel images of image region 122. In some embodiments, the high-speed camera includes a camera system having a frame rate of 25 kHz and resolution of 768×768 pixels. Such a camera is sufficiently fast to acquire 25 rounds of data acquisition in 1 millisecond. One skilled in the art will recognize, after reading this Specification, that the combination of a high-speed camera and image intensifier represents only one of several imager systems suitable for use with the present invention. Other suitable imagers include, without limitation, ultra-low-read-noise cameras (e.g., a single scientific CMOS camera, etc.), and the like.

Figure 5:
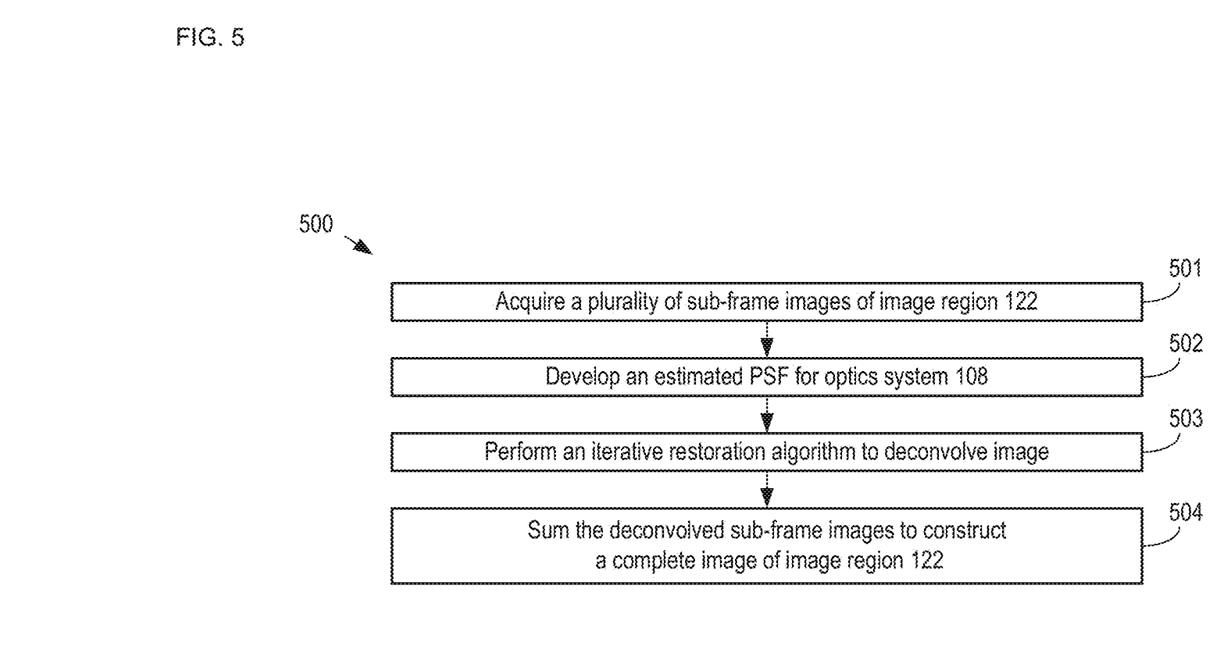
FIG. 5 depicts sub-operations suitable for use in operation 205.

As discussed below and with respect to method 500, it is advantageous that the camera of imager 112 include a frame trigger input such that accurate foci travel info can be developed for a plurality of sub-frames by synchronizing scanner 106 and the frame trigger.

Figure 4A:
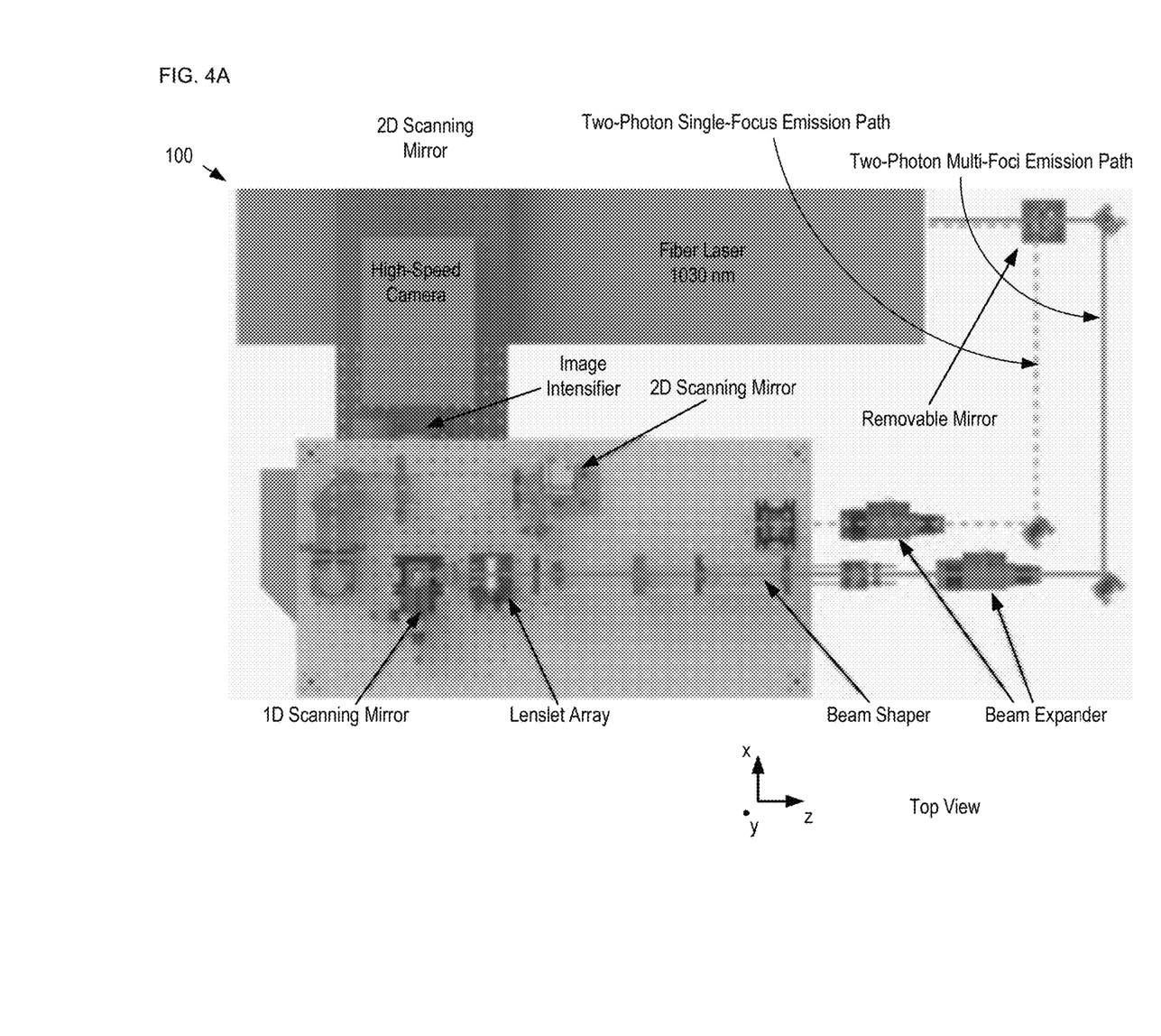
FIGS. 4A-B depict schematic drawings of top and front views, respectively, of imaging system 100, as well as the excitation paths through it.
Figure 4B:
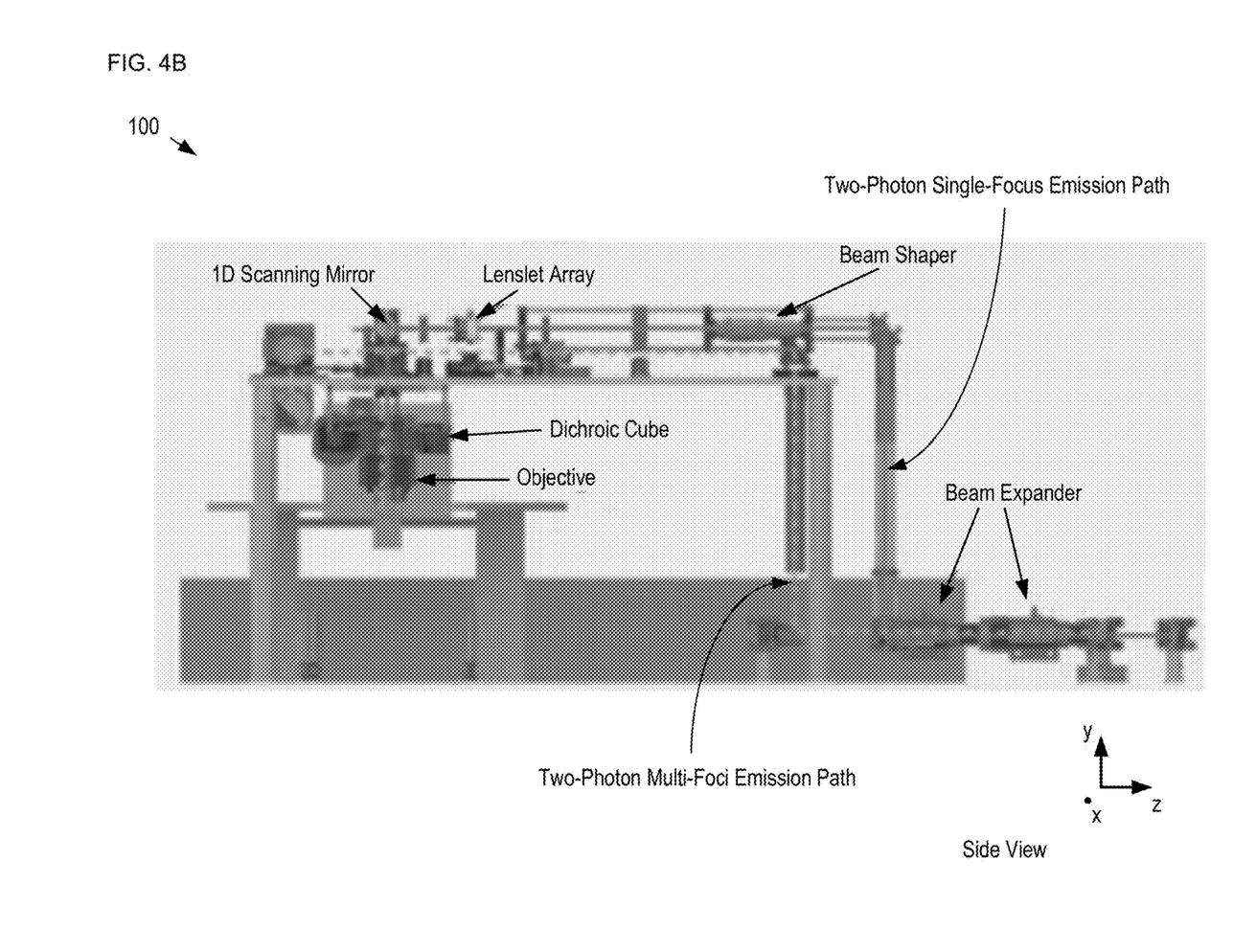
Figure 4C:
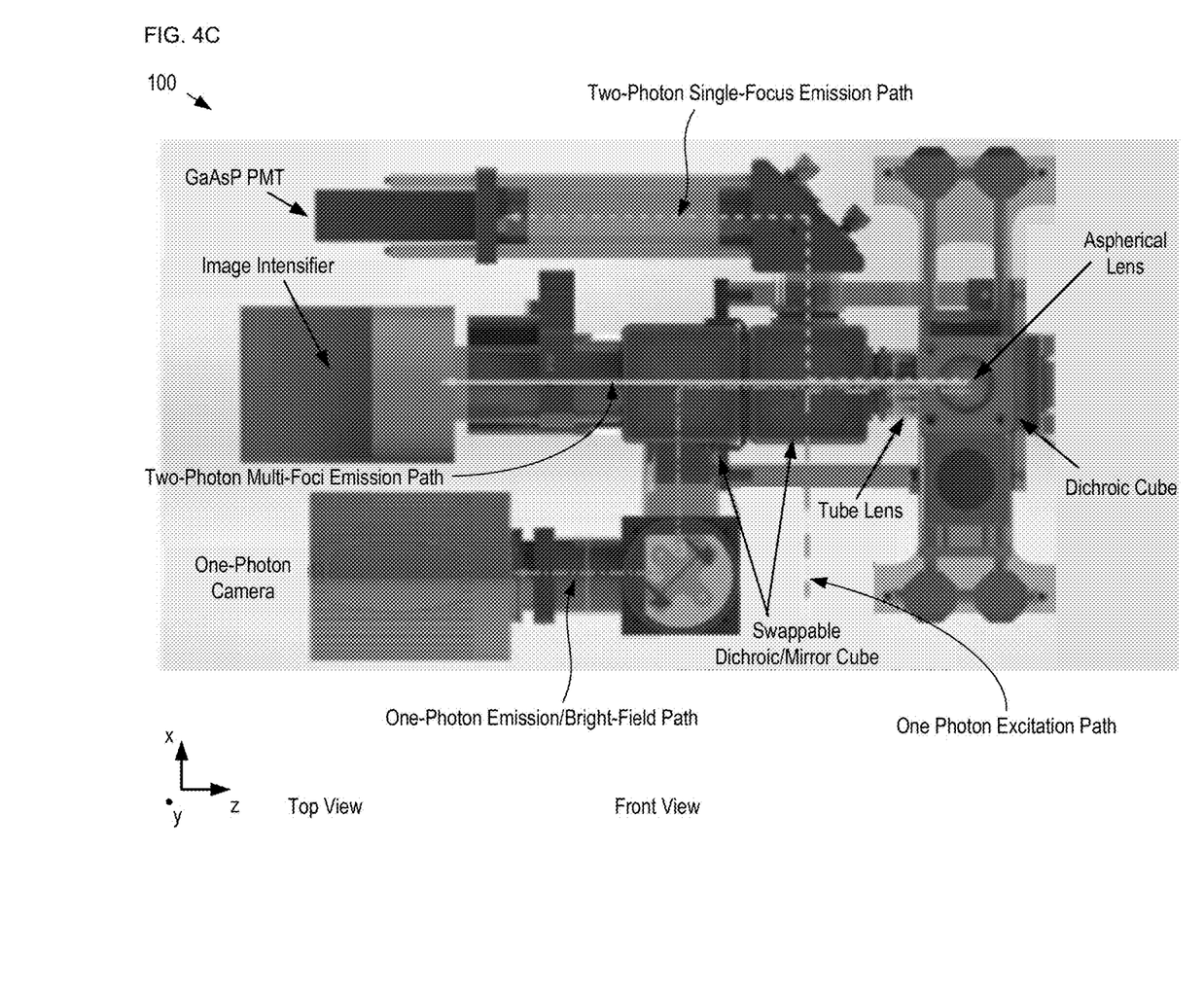
FIG. 4C depicts a top view of the optomechanics of system 100, as well as excitation and emission paths through it.

FIGS. 4A-B depict schematic drawings of top and front views, respectively, of imaging system 100, as well as the excitation paths through it. FIG. 4C depicts a top view of the optomechanics of system 100, as well as excitation and emission paths through it.

As shown in FIGS. 4A-C, a slider mechanism is provided to enable swapping of optical components for either the multi-foci path or conventional single-focus two-photon path. It should be noted that, in some embodiments, imaging system 100 enables one-photon imaging capability, which affords more versatile operation using a single imaging system.

It should further be noted that tissue scattering can lead to photons being emitted from different positions and overlapping into the same pixels at the camera of imager 112. This can lead to a blurred image. This phenomenon is particularly problematic when imaging in tissue to depths greater than a few hundred microns.

At operation 205, imager 112 passes output signal 126 to processor 128.

At operation 206, processor 128 reconstructs a fluorescence image of image region 122 from output signal 126 using a deconvolution algorithm. By using such an algorithm, a complete image frame can be reconstructed from multiple sub-frames while correcting for optical crosstalk between nearby foci. In some embodiments, the algorithm also provides spatial registration.

It is an aspect of the present invention that the post-processing routine included in operation 206 enables extraction of latent image information from a blurred image by utilizing both the photon excitation/emission position information and optical system information (i.e., the point-spread function of system 100).

FIG. 5 depicts sub-operations suitable for use in operation 206.

Operation 206 begins with sub-operation 501, wherein a plurality of sub-frame images are taken for each full frame image, where each sub-frame image captures a fraction of the foci travels. The number of sub-frame images taken can be any practical number, based on the capability of imager 112; however, the number of sub-frame images taken with present technology is typically within the range of approximately 10 to approximately 20. It should be noted that, as the number of sub-frame images taken increases, so does the amount of accurate foci position information that can be utilized for further deconvolution steps. Unfortunately, increasing the number of sub-frame images also decreases the photon signal obtained from each sub-frame image. It should be further noted that a practical limit on the number of sub-frame images normally arises from the upper limit on camera throughput/frame rate.

At sub-operation 502, a point-spread function (PSF) is estimated for image degradation induced by system 100. Deconvolution algorithms suitable for estimating the PSF are described by Biggs, et al., in "Acceleration of Iterative Image Restoration Algorithms," Applied Optics, Vol. 36, pp. 1766-1776 (1997), which is incorporated herein by reference. Estimation of the PSF is performed with the assistance of some prior knowledge on foci-position information and the processes by which the image of image region 122 is degraded. Exemplary degradation mechanisms include movement of image region 122 during imaging, misalignment within optics system 108 (e.g., out-of-focus lenses, optical element translation, etc.), signal-dependent noise, electronic noise, quantization noise, and the like. Image degradation can be modeled as:

$$g = h \otimes f + n \quad (1)$$

where f is the original undistorted image, g is the distorted noisy image, h is the PSF of system 100, $\otimes$ is the convolution operator, and n is the corrupting noise.

At sub-operation 503, the PSF developed in sub-operation 502 is used in an iterative reconstruction algorithm that is applied to the rest of the sub-images. Reconstruction algorithms suitable for use with the present invention include, without limitation, Richardson-Lucy deconvolution, maximum-entropy deconvolution, Gerchberg-Saxton magnitude and phase retrieval algorithms, and the like. In the illustrative embodiment, a specialized Richardson-Lucy deconvolution algorithm is applied to the rest of the sub-images in sub-operation 503.

In accordance with the present invention, an iterative reconstruction algorithm is expressed as:

$$\hat{f}_{k+1} = f \cdot M_i \left( h * \frac{g}{h \otimes \hat{f}_k} \right), \quad (2)$$

where $\hat{f}_k$ is the estimate of f after k iterations, * is the correlation operator, and $M_i$ is a foci-position mask for sub-frame i. It should be noted that accurate foci travel info can be developed for each sub-frame i synchronizing scanner 106 and a frame trigger applied to the camera of imager 112. As a result, each iteration step of the estimation excludes any non-zero results for any pixel outside the foci position mask. Typically, the foci-position mask, $M_i$, for each sub-frame i is obtained during an offline calibration routine. A non-limiting example of a suitable calibration routine includes imaging the surface of a known, uniform fluorescence source, such as Uranium compound glass, using system 100 where the system has a synchronized triggering signal, and acquiring the foci-position mask for each sub-frame directly at imager 112.

At sub-operation 504, processor 128 sums the sub-images that have been through sub-operation 503 to form a complete fluorescence image of image region 122.

Figure 6A:
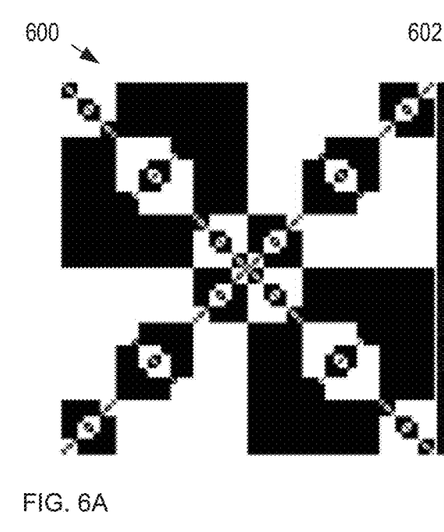
FIGS. 6A-C depict images of a test specimen before deconvolution, after computation assembly of raw sub-images, and after application of the complete deconvolution routine, respectively.
Figure 6B:
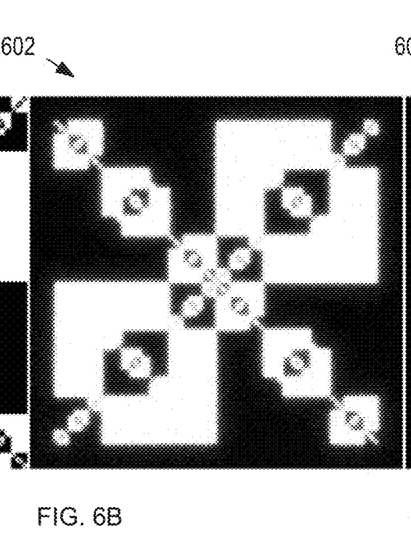
Figure 6C:
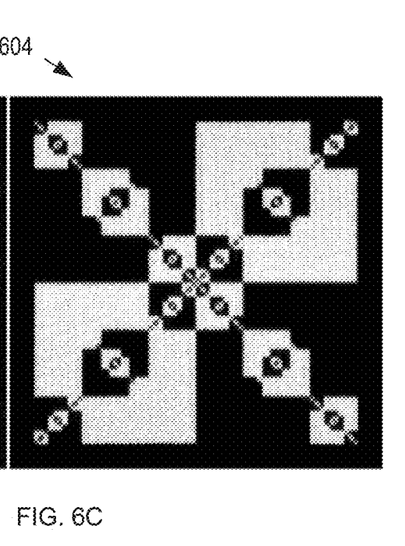

FIGS. 6A-C depict images of a test specimen before deconvolution, after computation assembly of raw sub-images, and after application of the complete deconvolution routine, respectively. Images 600-602 are obtained after light propagation through 250 microns of brain tissue. Careful examination of images 600-602 reveals that many of the finer features of test image 600 are restored in image 602.

One skilled in the art will recognize that the proposed deconvolution routine requires heavy data-transfer and computation workload. Conventional state-of-the-art cameras are limited to recording only a few seconds of video under typical operating conditions of imaging system 100.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. An imaging system comprising:
    a source operative for providing a first plurality of light signals the first plurality of light signals being arranged such that they form a two-dimensional array of foci at an image region that defines a first plane;
    a single-axis scanner operative for linearly scanning the first plurality of light signals along a first direction in the first plane such that each light signal of the first plurality thereof interrogates a different one of a plurality of sub-image regions, wherein the first plurality of light signals is arranged as the two-dimensional array having a first periodicity in a second direction in the first plane and a second periodicity in a third direction in the first plane, and wherein the two-dimensional array is oriented such that the second direction and first direction form a first non-zero, acute angle, θ, within the first plane, and further wherein the plurality of sub-image regions are arranged in a two-dimensional arrangement within the image region; and
    a detector operative for detecting a second plurality of light signals, wherein each of the second plurality of light signals is generated in response to absorption of optical energy from at least one of the first plurality of light signals.

2. The imaging system of claim 1, wherein at least one of the first periodicity and second periodicity enables an image resolution for the imaging system that is less than or equal to two microns.

3. The imaging system of claim 1, wherein at least one of the first periodicity and second periodicity enables an image resolution for the imaging system that is less than or equal to one micron.

4. The imaging system of claim 1, wherein the two-dimensional array includes N first light signals in the second direction, and wherein θ=arctan(1/N).

5. The imaging system of claim 1 wherein the source comprises an ultrashort-pulsed regenerative fiber laser amplifier.

6. The imaging system of claim 1 wherein the first plurality of light signals have substantially the same intensity.

7. The imaging system of claim 1 wherein the detector comprises a camera and an image intensifier.

8. The imaging system of claim 1 wherein the imaging system is characterized by a point-spread function, and wherein the imaging system further comprises a processor that is operative for reconstructing an image of the first plane based on the position of a first light signal of the first plurality of light signals within its corresponding sub-region and the point-spread function.

9. A method for forming an image of an image region, the method comprising:

providing a plurality of first light signals as a two-dimensional array having a first periodicity in a first direction in a first plane and a second periodicity in a second direction in the first plane;

orienting the two-dimensional array such that the first direction and a third direction form a first non-zero, acute angle, θ, within the first plane;

scanning the plurality of first light signals along the third direction in the first plane, wherein each of the plurality of first light signals interrogates a different sub-region of the image region;

detecting at least one second light signal that is generated within the image region;

reconstructing a sub-image of each of the plurality of sub-regions based on second light signals generated within that sub-region; and combining the plurality of sub-images.

10. The method of claim 9 further comprising providing an imaging system that is operative for detecting the at least one second light signal, wherein at least one of the first periodicity and second periodicity enables an image resolution for the imaging system that is less than or equal to two microns.

11. The method of claim 10, wherein at least one of the first periodicity and second periodicity enables an image resolution for the imaging system that is less than or equal to one micron.

12. The method of claim 9, wherein the two-dimensional array includes N first light signals in the first direction, and wherein θ=arctan(1/N).

13. The method of claim 9, further comprising providing a source for providing the plurality of first light signals, wherein the source comprises an ultrashort-pulsed regenerative fiber laser amplifier.

14. The method of claim 9, further comprising providing a source for providing the plurality of first light signals such that they have substantially the same intensity.

15. The method of claim 9, further comprising providing an imaging system that is operative for detecting the at least one second light signal, wherein the imaging system is characterized by a point-spread function, and wherein each sub-image is reconstructed based on the position of a first light signal of the plurality of first light signals within its corresponding sub-region and the point-spread function.

16. The method of claim 9, wherein each of the plurality of sub-images is reconstructed by operations comprising:

forming a first estimate, $\hat{f}_i$, of the sub-image, where i=1;

for i=1 through K, forming an iterated estimate, $\hat{f}_{i+1}$, of the sub-image, where the iterated estimate is formed based on a previous estimate, $\hat{f}_i$, and a plurality of foci-position masks that correspond to foci-positions within the corresponding sub-region.

17. The method of claim 16, wherein the iterated estimate, $\hat{f}_{i+1}$, is formed as $$\hat{f}_{i+1} = f \cdot M_j \left( h * \frac{g}{h \otimes \hat{f}_i} \right),$$

where $f \cdot M_j$ is the dot product of f and $M_j$, and j is equal to 1 through N, N being the number of foci-positions within the corresponding sub-region.

* * * * *